(12) United States Patent
Altshuler et al.

(10) Patent No.: US 6,511,475 B1
(45) Date of Patent: *Jan. 28, 2003

(54) HEADS FOR DERMATOLOGY TREATMENT

(75) Inventors: Gregory B. Altshuler, Beverly, MA (US); R. Rox Anderson, Lexington, MA (US)

(73) Assignees: The General Hospital Corporation, Boston, MA (US); Palomar Medical Technologies, Inc., Burlington, MA (US)

(*) Notice: Subject to any disclaimer, the term of this patent is extended or adjusted under 35 U.S.C. 154(b) by 10 days.

This patent is subject to a terminal disclaimer.

(21) Appl. No.: 09/634,981

(22) Filed: Aug. 9, 2000

Related U.S. Application Data

(63) Continuation of application No. 09/078,055, filed on May 13, 1998.
(60) Provisional application No. 60/046,542, filed on May 15, 1997, and provisional application No. 60/077,726, filed on Mar. 12, 1998.

(51) Int. Cl.[7] .............................................. A61B 18/18
(52) U.S. Cl. .................................. 606/9; 606/2; 606/23
(58) Field of Search ........................... 606/2, 9, 23, 27, 606/28, 31–33, 39, 40–42, 47–50, 1, 13, 15, 20, 21

(56) References Cited

U.S. PATENT DOCUMENTS

| | | |
|---|---|---|
| 3,327,712 A | 6/1967 | Kaufman |
| 3,527,932 A | 9/1970 | Thomas |
| 3,538,919 A | 11/1970 | Meyer |
| 3,622,743 A * | 11/1971 | Muncheryan .......... 219/121.62 |
| 3,693,623 A | 9/1972 | Harte et al. |
| 3,818,914 A | 6/1974 | Bender |
| 3,834,391 A | 9/1974 | Block |
| 3,900,034 A | 8/1975 | Katz et al. |
| 4,233,493 A | 11/1980 | Nath |
| 4,316,467 A | 2/1982 | Muckerheide |
| 4,388,924 A | 6/1983 | Weissman et al. |
| 4,461,294 A | 7/1984 | Baron |
| 4,539,987 A | 9/1985 | Nath et al. |
| 4,608,978 A | 9/1986 | Rohr |
| 4,617,926 A | 10/1986 | Sutton |
| 4,718,416 A | 1/1988 | Nanaumi |
| 4,733,660 A * | 3/1988 | Itzkan .................... 219/121.79 |
| 4,747,660 A | 5/1988 | Nishioka |
| 4,819,669 A | 4/1989 | Politzer |

(List continued on next page.)

FOREIGN PATENT DOCUMENTS

| | | |
|---|---|---|
| AT | 400 305 B | 4/1995 |
| DE | 3837248 A | 5/1990 |
| EP | 0 142 671 | 5/1985 |

(List continued on next page.)

OTHER PUBLICATIONS

Altshuler, Grigory B., et al., "Acoustic response of hard dental tissues to pulsed laser action," *SPIE*, vol. 2080, Dental Applications of Lasers (1993), pp. 97–103.

(List continued on next page.)

Primary Examiner—Roy D. Gibson
(74) Attorney, Agent, or Firm—Wolf, Greenfield & Sacks, P.C.

(57) ABSTRACT

Methods and apparatus for dermatology treatment are provided which involve the use of continuous wave (CW) radiation, preheating of the treatment volume, precooling, cooling during treatment and post-treatment cooling of the epidermis above the treatment volume, various beam focusing techniques to reduce scattering and/or other techniques for reducing the cost and/or increasing the efficacy of optical radiation for use in hair removal and other dermatological treatments. A number of embodiments are included for achieving the various objectives indicated above.

73 Claims, 6 Drawing Sheets

U.S. PATENT DOCUMENTS

| | | |
|---|---|---|
| 4,832,024 A | 5/1989 | Boussignac |
| 4,860,172 A | 8/1989 | Schlager et al. |
| 4,860,744 A | 8/1989 | Johnson et al. |
| 4,917,084 A | 4/1990 | Sinofsky |
| 4,926,227 A | 5/1990 | Jensen |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,282,797 A * | 2/1994 | Chess .......... 606/13 |
| 5,300,097 A | 4/1994 | Lerner et al. |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,348,551 A | 9/1994 | Spears et al. |
| 5,350,376 A | 9/1994 | Brown |
| 5,380,317 A | 1/1995 | Everett et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,519,534 A | 5/1996 | Smith et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,662,644 A | 9/1997 | Swor |
| 5,683,380 A | 11/1997 | Eckhouse |
| 5,698,866 A | 12/1997 | Doiron et al. |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse |
| 5,853,407 A | 12/1998 | Miller |
| 5,885,273 A | 3/1999 | Eckhouse |
| 5,885,274 A | 3/1999 | Fullmer et al. |
| 5,944,748 A | 8/1999 | Mager et al. |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 6,015,404 A | 1/2000 | Altshuler et al. |
| 6,027,495 A * | 2/2000 | Miller .......... 606/9 |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,080,146 A | 6/2000 | Altshuler et al. |
| 6,096,029 A | 8/2000 | O'Donnell, Jr. |
| 6,096,209 A | 8/2000 | O'Brien et al. |
| 6,104,959 A | 8/2000 | Spertell |
| 6,280,438 B1 | 8/2000 | Eckhouse et al. |
| 6,120,497 A * | 9/2000 | Anderson et al. .......... 606/2 |
| 6,149,644 A | 11/2000 | Xie |
| 6,174,325 B1 | 1/2001 | Eckhouse |
| 6,197,020 B1 * | 3/2001 | O'Donnell, Jr. .......... 606/13 |
| 6,273,884 B1 | 8/2001 | Altshuler et al. |
| 6,273,885 B1 | 8/2001 | Koop et al. |

FOREIGN PATENT DOCUMENTS

| | | |
|---|---|---|
| EP | 0 565 331 | 10/1993 |
| EP | 0 724 894 | 8/1996 |
| EP | 0 726 083 | 8/1996 |
| EP | 0 736 308 | 10/1996 |
| EP | 0 755 698 | 1/1997 |
| EP | 0 763 371 | 3/1997 |
| EP | 0 765 673 | 4/1997 |
| EP | 0 765 674 | 4/1997 |
| EP | 0 783 904 A2 | 7/1997 |
| EP | 1038505 A2 | 9/2000 |
| FR | 2 591 902 | 7/1987 |
| GB | 2 044 908 A | 10/1980 |
| GB | 2 123 287 A | 2/1982 |
| GB | 2360946 A | 10/2001 |
| RU | 95105406 | 6/1997 |
| RU | 94012665 | 10/1997 |
| RU | 94040344 | 10/1997 |
| RU | 95102749 | 11/1997 |
| RU | 4954402 | 10/1998 |
| SU | 532304 | 7/1974 |
| SU | 719439 | 8/1975 |
| SU | 741747 | 10/1977 |
| SU | 1257475 A1 | 9/1986 |
| SU | 13269632 A1 | 7/1987 |
| WO | 00/74781 A1 | 12/0000 |
| WO | WO 86/02783 | 5/1986 |
| WO | WO 90/00420 | 1/1990 |
| WO | WO 92/16338 | 10/1992 |
| WO | WO 92/19165 | 11/1992 |
| WO | WO 93/05920 A1 | 4/1993 |
| WO | WO 95/15725 A1 | 6/1995 |
| WO | WO 95/32441 A1 | 11/1995 |
| WO | WO 96/23447 A1 | 8/1996 |
| WO | WO 96/25979 A1 | 8/1996 |
| WO | WO 97/13458 | 4/1997 |
| WO | WO 98/04317 | 2/1998 |
| WO | WO 98/24507 | 6/1998 |
| WO | WO 98/51235 A1 | 11/1998 |
| WO | WO 98/52481 A1 | 11/1998 |
| WO | WO 99/29243 A1 | 6/1999 |
| WO | WO 99/38569 A3 | 8/1999 |
| WO | WO 99/38569 A2 | 8/1999 |
| WO | WO 99/46005 A1 | 9/1999 |
| WO | WO 00/03257 A1 | 1/2000 |
| WO | WO 01/03257 A1 | 1/2001 |
| WO | WO 01/34048 | 5/2001 |
| WO | WO 01/42671 A1 | 6/2001 |

OTHER PUBLICATIONS

Altshuler, G. B., et al., "Extended Theory of Selective Photothermolysis," *Lasers in Surgery and Medicine*, 29: 416–432 (2001).

Amy, Robert L. and Storb, R., "Selective Mitochondrial Damage by a Ruby Laser Microbeam: An Electron Microscopic Study," *Science*, 15:756–758, Nov. 1965.

Anderson, R. Rox, et al., "The Optics of Human Skin," *The Journal of Investigative Dermatology*, vol. 77, No. 1, pp. 13–19, 1981.

Anderson, R. R, and Parrish, J. A., M.D., "Selective Photothermolysis: Precise Microsurgery by Selective Absorption of Pulsed Radiation," *Science*, 220:524–527, 1983.

Belikov, A. V., et al., "Identification of enamel and dentine under tooth laser treatment," *SPIE*, Progress in Biomedical Optics, Europt Series, Proceedings of Medical Applications of Lasers III, vol. 2623, pp. 109–116.

Dover, J. S., et al., "Pigmented Guinea Pig Skin Irradiated with Q–Switched Ruby Laser Pulses," *Arch Dermatol*, 125:43–49, 1989.

Finkelstein, L. H. and Blatstein, Lee M., "Epilation of Hair–Bearing Urethral Grafts Using the Neodymium: YAG Surgical Laser," *The Journal of Urology*, 146:840–842, 1991.

Goldman, L., "Laser History and Theory," "Laser Instrumentation," and "Summary and Conclusions," Biomedical Aspects of the Laser, New York, Springer–Verlag, 1967, pp iii–11, 220–232.

Goldman, L., "Dermatologic Manifestation of Laser Radiation," *Fed Am Soc Exp Biology*, Suppl. 14:S–92–S–93, 1965.

Goldman, L., "Effects on New Laser Systems on the Skin," *Arch Dermatol*, 108: 385–390, 1973.

Goldman, L., "Laser Surgery for Skin Cancer," *NY State J Med*, 77:1897–1900, 1977.

Goldman, L., "Surgery by Laser for Malignant Melanoma," *J Dermatol. Surg. Oncol.*, 5(2):141–144, 1979.

Goldman, L., "The Skin," *Arch Environ Health*, 18:434–426, 1969.

Goldman, L. and Richfield, D. F., "The Effect of Repeated Exposures to Laser Beams," *Acta Derm.–Veneoral*, 44:264–268, 1964.

Goldman, L. and Rockwell, J., "Laser Action at the Cellular Level," *JAMA*, 198:641–644, 1966.

Goldman, L. and Wilson, R. G., "Treatment of Basal Cell Epithelioma by Laser Radiation," *JAMA*, 189:773–775, 1964.

Goldman, L., et al., "Biomedical Aspects of Lasers," *JAMA*, 188:230–234, 1964.

Goldman, L., et al., "Effect of the Laser Beam on the Skin: Preliminary and Short Report," *The Journal of Investigative Dermatology*, 40:121–122, 1963.

Goldman, L., et al., "Effect of the Laser Beam on the Skin III. Exposure of Cytological Preparations," *The Journal of Investigative Dermatology*, 42:247–251, 1964.

Goldman, L., et al., "Impact of the Laser on Nevi and Melanomas," *Arch Dermatol*, 90:71–75, 1964.

Goldman, L., et al., "Laser Treatment of Tattoos," *JAMA*, 210:163–166, 1967.

Goldman, L., et al., "Long–Term Laser Exposure of a Senile Freckle," *Arch Environ Health*, 22:401–403, 1971.

Goldman, L., et al., "Pathology of the Effect of the Laser Beam on the Skin," *Nature*, 197:912–914, 1963.

Goldman, L., et al., "Preliminary Investigation of fat Embolization from Pulsed Ruby Laser Impacts of Bone," *Nature*, 221:361–363, 1969.

Goldman, L., et al., "Radiation from a Q–Switched Ruby Laser. Effect of Repeated Impacts of Power Output of 10 Megawatts on a Tattoo of Man," *The Journal of Investigative Dermatology*, 44:69–71, 1965.

Goldman, L., et al., "Replica Microscopy and Scanning Electron Microscopy of Lawer Impacts on the Skin," *The Journal of Investigative Dermatology*, 52:18–24, 1969.

Grossman, M. C., et al., "Damage to Hair Follicles by Normal–mode Ruby Laser Pulses," *Journal of the American Academy of Dermatology*, 35(6):889–894, 1996.

Grossman, M. C., et al., "Laser Targeted at Hair Follicles," *Lasers Med Surg.*, Suppl. 7:221, 1995.

Klein, E., et al., "Biological Effects of Laser Radiation I: Threshold Studies and Reversible Depigmentation in Rodent Skin," *Northeast Electronics Research and Engineering Meeting—NEREM Record–1965*, IEEE Catalogue No. F–60, (Nov. 4, 1965) pp. 108–109.

Kuhns, J. G., et al., "Biological Effects of Laser Radiation II: Effects of Laser Irradiation on the Skin," *Northeast Electronics Research and Engineering Meeting—NEREM Record 1965*, IEEE Catalogue No. F–60, (Nov. 4, 1965) pp. 152–153.

Kuhns, James G., et al., "Laser Injury in Skin," *Laboratory Investigation*, vol. 17, No. 1, (Jul. 1967) pp. 1–13.

Manstein, Dieter, et al., "Selective Photothermolysis of Lipid–Rich Tissue," *American Society for Laser Medicine and Surgery Abstracts*, No. 17, American Society for Laser Medicine and Surgery Twenty–First Annual Meeting, Apr. 20–22, 2001, p. 6.

Margolis, R. J., et al., "Visible Action Spectrum for Melanin–Specific Selective Photothermolysis," *Lasers in Surgery and Medicine*, 9:389–397, 1989.

Parrish, J. A., M.D., et al., "Selective Thermal Effects with Pulsed Irradiation from Lasers: From Organ to Organelle," *The Journal of Investigative Dermatology*, 80:75s–80s, 1983.

Polla, L. L. et al., "Melanosomes Are a Primary Target of Q–Switched Ruby Laser Irradiation in Guinea Pig Skin," *The Journal of Investigative Dermatology*, 89:281–286, 1987.

Riggle, Grant C., "Laser Effects on Normal and Tumor Tissue," *Laser Applications in Medicine and Biology*, 1:35–63, 1971.

Shimbashi, T. and Kojima, T., "Ruby Laser Treatment of Pigmented Skin Lesions," *Aesthetic Plastic Surgery*, 19:225–229, 1995.

Stratton, K., et al., "Biological Effects of Laser Radiation II: ESR Studies of Melanin Containing Tissues after Laser Irradiation," *Northeast Electronics Research and Engineering Meeting—NEREM Record–1965*, IEEE Catalogue, No. F–60, (Nov. 4, 1965) pp. 150–151.

Taylor, C. R., et al., "Treatment of Tattoos by Q–Switched Ruby Laser," *Arch Dermatol*, 126:893–899, 1990.

Tuchin, Valery V., "Laser Light Scattering in Biomedical Diagnostics and Therapy," reprinted from *Journal of Laser Applications*, vol. 5(2,3), pp. 43–60 (Fall 1993) Laser Institute of America, Toledo, Ohio.

Watanabe, S., et al., "Comparative Studies of Femtosecond to Microsecond Laser Pulses on Selective Pigmented Cell Injury in Skin," *Photochemistry and Photobiology*, 53:757–762, 1991.

Watanabe, S., et al., The Effect of Pulse Duration on Selective Pigmented Cell Injury by Dye Lasers, *The Journal of Investigative Dermatology*, 88:523, 1987.

Welch, A. J., et al., "Evaluation of Cooling Techniques for the Protection of the Epidermis during ND–YAG Laser Irradiation of the Skin," *Neodymium–YAG Laser in Medicine and Surgery*, New York, Elsevier, 1983, pp 196–204.

Yules, R. B., et al., "The Effect of Q–Switched Ruby Laser Radiation on Dermal Tattoo Pigment in Man," *Arch Surg*, 95:179–180, 1967.

Zeitler, E. and Wolbarsht, M. L., "Laser Characteristics that Might be Useful in Biology," *Laser Applications in Medicine and Biology*, 1:1–16, 1971.

\* cited by examiner

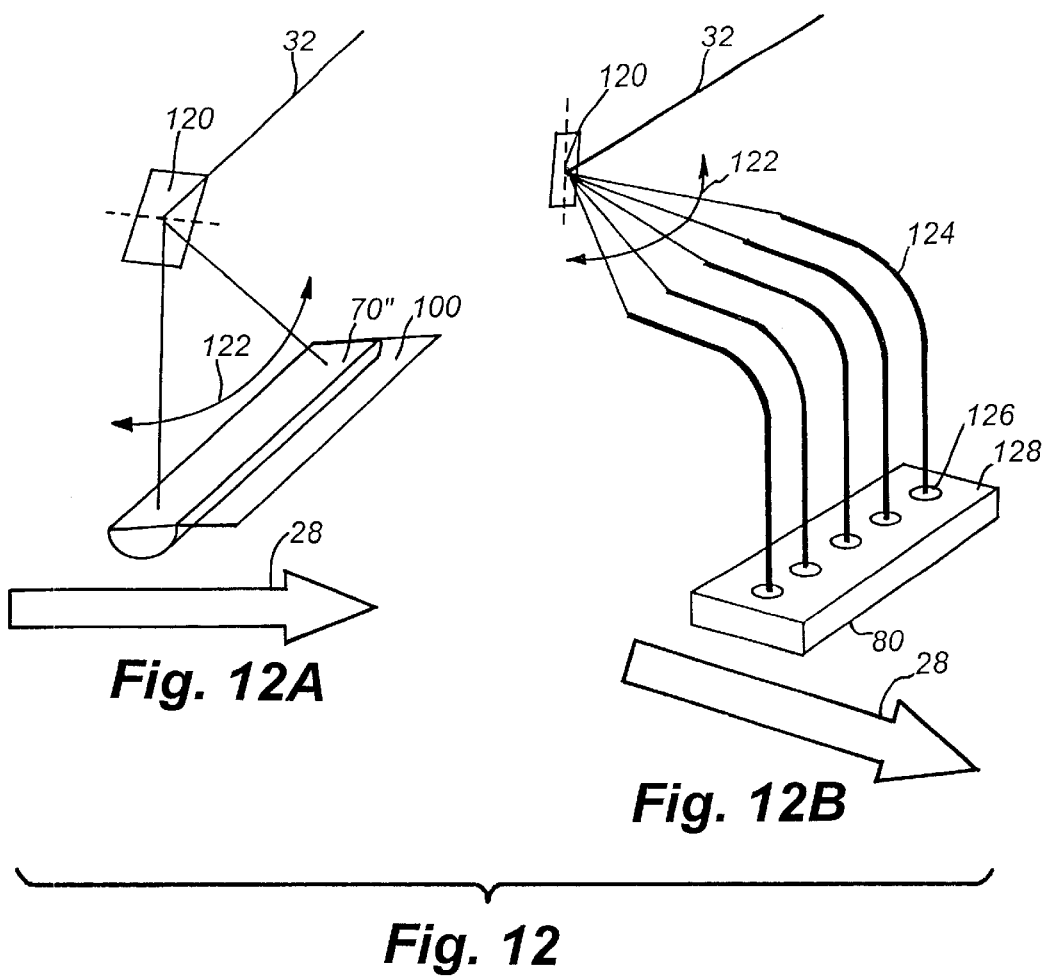
Fig. 12A
Fig. 12B
Fig. 12
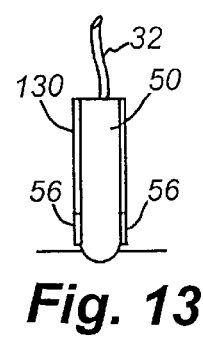
Fig. 13

HEADS FOR DERMATOLOGY TREATMENT

RELATED APPLICATIONS

This application is a continuation of application Ser. No. 09/078,055, filed May 13, 1998, entitled Method and Apparatus for Dermatology Treatment which application claims priority from provisional specifications 60/046,542 filed May 15, 1997 and 60/077,726 filed Mar. 12, 1998, the subject matter of which are incorporated herein by reference.

FIELD OF THE INVENTION

This invention relates to apparatus for using optical radiation to treat dermatological problems and, more particularly, to heads for such apparatus which heads provide an elongated focus area at a selected depth and/or selected preconditioning, for example heating and/or cooling, of a treatment area.

BACKGROUND OF THE INVENTION

Lasers, lamps, and other sources of electromagnetic radiation, particularly in the optical wavebands, are being increasingly utilized for various dermatological treatments and, in particular, for the removal of unwanted hair, spider veins, leg veins, other veins or other blood vessels which are visible through the patient's skin, lesions, port-wine stains, tattoos, and the like. In performing such treatments, it is desirable that the cost for the treatment be kept as low as possible, consistent with achieving desired results, and that risk of injury to the patient be minimized.

Since continuous wave (CW) lasers and other CW radiation sources are typically substantially less expensive than pulsed sources of comparable wavelength and energy, for cost reasons, it would be preferable to use CW sources rather than pulsed sources for such dermatological treatments. However, in order to avoid injury to the patient, the duration of energy application to a given area of the patient's skin must be controlled, this generally resulting in the more expensive pulsed light sources being used for the various dermatological treatments.

Further, since the only way to get radiation to areas where treatment is desired, which areas are normally in the dermis, is to transmit the radiation to such area through the overlying epidermis, some portion of incident radiation is absorbed in the epidermis creating the potential for damage thereto. This is a particular problem where melanin is being targeted in the dermis, as is for example the case for various hair removal treatments, since there is a substantial concentration of melanin in the lower portion of the epidermis at the dermal/epidermal (DE) junction. Further, the deeper in the dermis that treatment is desired, and/or the larger the element being treated, the more energy must be used, this generally involving the use of a more powerfull laser or other radiation source and/or operating such source for longer time durations. This further increases the potential for epidermal damage.

Some attempts have been made in the past to scan a CW radiation source, such as the laser, over a treatment area, which has been done with the radiation source spaced from the skin in order to facilitate movement of the source. However, techniques currently utilized for protecting the epidermis frequently involve contact cooling of the epidermis and, for certain treatments such as hair removal, performing the treatment with pressure applied to the patient's skin is also desirable. Irradiation by use of a head in contact with the skin also permits more efficient transfer of energy into the patient's skin, thereby reducing the size of the source required for a given treatment energy density and, therefore, reducing the cost of such source. This cost could be further reduced if the radiation source is not the only source being utilized to heat the area under treatment.

Another problem in performing laser dermatology treatments, particularly when such treatment is to be performed over an area larger than the optical aperture of the applicator being utilized, is to obtain substantially uniform irradiation over the area so that sufficient radiation is applied to all portions of the area to achieve the desired treatment, while no portion of the area has so much radiation applied thereto as to cause thermal damage to the skin. Such uniform irradiation is very difficult with a pulsed source which typically utilize a circular aperture. Typically, the procedure followed is to irradiate a spot with a given pulse and to then reposition the head to an adjacent spot for irradiation. If the spots do not overlap, there will be portions of the area under treatment which do not receive radiation and, unfortunately, the radiation output is frequently not uniform over the entire optical aperture, being greater near the center, and less at the edges. Therefore, there is generally some overlap between adjacent spots. However, this results in some portions of the area under treatment receiving at least a double dose of radiation, which poses a potential danger of thermal damage in these overlap areas. Substantially uniform irradiation of a treatment area is therefore virtually impossible with a pulsed radiation source utilizing existing techniques.

Another problem which increases the energy required from the radiation source utilized is that, for existing systems, heating of the target to achieve the desired therapeutic effect is accomplished solely by radiation from the radiation source. If the temperature of the target could be increased by some type of preheating of the target volume, the amount of energy required from the radiation source to complete the job would be substantially reduced. However, such preheating must be achieved in a way such that the cost of such preheating is not greater than the savings achieved by reduced requirements on the radiation source.

Similarly, in order to protect the epidermis, many procedures require that the epidermis be cooled, preferably to the DE junction, to at least a selected temperature, for example 10° C., 0° C., or even slightly lower, before radiation is applied. If contact cooling starts when the head is over the target area, this means that there is some delay, perhaps half a second to a second, between the time the head is applied to the patient's skin and the time the radiation source is fired. With CW, such a delay once the radiation source is over the target area is difficult to achieve and it is therefore preferable that precooling of the epidermis occur for the target area before the radiation source is thereover. An ideal procedure would be to preheat the skin down to the target depth and then to precool to the DE junction, leaving the target depth preheated. Mechanisms in general, and heads in particular, for achieving such precooling and/or preheating followed by precooling have not heretofore existed.

It is also desirable to be able to focus the optical radiation at substantially the target depth. While heads have heretofore existed which are capable of achieving such a focus on a given spot, faster operation, particularly when operating in CW mode, although also when operating in pulse mode under some circumstances, can be achieved if there is a line focus at the target depth rather than a point focus. Mechanisms for achieving such a line focus have also not heretofore existed.

A need therefore exists for improved apparatus for utilizing optical radiation to treat various dermatological conditions, and in particular, improved heads for use in such apparatus which facilitate preheating and/or precooling of the target area, particularly when operating in CW mode, but also when operating in other modes, and which also facilitate achieving of a line focus for the radiation at a selected target depth for enhanced, and in particular, more rapid treatment.

SUMMARY OF THE INVENTION

In accordance with the above, this invention provides various heads for use in apparatus for effecting a selected dermatologic treatment in an area of a patient's skin. For some embodiments, the head includes a block formed of a material having good thermal transfer properties, a plurality of first optical waveguide elements and a plurality of second optical waveguide elements extending through the block, the first and second optical waveguide elements being angled at first and second angles respectively, which angles are selected so that light passing through the first and second optical waveguide elements converge at a selected depth. The optical waveguide elements have radiation applied thereto which is appropriate for the selected dermatologic treatment. The selected depth is in the area under treatment at which the dermatologic treatment is to occur. For some embodiments, a recess is formed in a surface of the head in contact with the patient's skin, the recess being at the distal end of the optical waveguide elements, and the selected depth is at a selected location in the recess. For these embodiments, a means is provided for moving skin in the area under treatment into said recess as said recess passes thereover. This means may, for example, include a source of negative pressure connected to the recess. For preferred embodiments, the block also has a skin contacting surface which retroreflects radiation leaving the patient's skin. A mechanism may also be provided for controlling the temperature of either the entire block or selected portions thereof.

For other embodiments, the head includes an astigmatic lens having an elongated outer surface, one side of said surface contacting the patient's skin in the area to be treated along an elongated line. A mechanism is provided which delivers light of a wavelength suitable for the dermatologic procedure to the lens on a side thereof other than the side contacting the patient's skin, the lens focusing light delivered thereto to a selected depth in the patient's skin. The lens may be a cylindrical lens with a diameter such that light delivered thereto is focused to the selected depth, and may be mounted to be either stationary or rotating as the head is moved over a treatment area. For some embodiments, the lens is treated so as to normally have total internal reflection, the total internal reflection being broken at a surface of the lens in contact with the patient's skin. To achieve the desired focus, the radius of curvature of the cylindrical lens for some embodiments is less than or equal 10 mm. For some embodiments, the selected depth is that for a portion of a hair follicle responsible at least in part for hair growth, for example, the hair bulge or the hair bulb. The selected depth may, for example, be 1 mm to 5 mm.

The mechanism for delivering light to the lens may deliver light along a line substantially parallel to the elongated line contacting the patient's skin surface and/or may cause light to be delivered to the lens at a variety of angles. A cooling mechanism may also be available for the patient's skin before the lens makes contact with the skin and/or while the lens is in such contact, the cooling mechanism for some embodiments, including a mechanism for cooling the lens. For some embodiments, the lens focuses light at said selected depth to an astigmatic focus area having a long dimension substantially parallel to the elongated line of lens contact with the skin. Finally, for some embodiments, the mechanism delivering light to the lens scans along the lens in its elongated direction, the scanning being at a selected rate.

More generally, the invention includes a focusing element having a light receiving region, a light delivery region which is adapted to be in contact with the patient's skin and a region which focuses light entering at said receiving region, the focus, when such element is in contact with the patient's skin being to an elongated astigmatic focus area at a selected skin depth. A mechanism is included which delivers light of a wavelength suitable for the dermatologic procedure to the light receiving region. The selected depth for some embodiments is the depth for a portion of a hair follicle responsible at least in part for hair growth, for example the hair bulge and/or hair bulb, and may be approximately 1 mm to 5 mm into the skin. A cooling mechanism for the patient's skin may also be provided, which mechanism is operated before the element makes contact with the skin and/or while the element is in contact therewith.

In accordance with still another embodiment of the invention, the head includes an optically transparent channel for delivering optical radiation of a wavelength appropriate for effecting the treatment in the area, a head portion of a thermally conductive material mounted relative to the channel so that it moves over each segment to be treated of such area before the channel, and a thermal component which controls the temperature of the head portion, and thus of each skin segment prior to treatment. In particular, the component may cool the portion, and thus each skin segment prior to treatment and/or the component may heat the portion, and thus heat each segment prior to treatment. The head may include a block formed of a material having good heat transfer properties, the block being adapted to move over the area during treatment, the channel being formed through the block and the portion being a portion of the block which is forward of the channel as the block is moved over the area. The head portion forward of the channel may be divided into a first thermally conductive portion which is heated and a second thermally conductive portion which is cooled, which portions are thermally insulated from each other, the first portion heating the patient's skin to the depth where treatment is to be performed and the second portion then cooling the patient's epidermis prior to irradiation. The head may also include a portion of a thermally conductive material mounted relative to the channel so that it moves over each segment to be treated of the area after the channel; and a thermal component which cools such rear head portion, and thus each skin segment after treatment.

While for preferred embodiments, preheating of the skin in the treatment area is accomplished in conjunction with the use of CW radiation and movement of the head over the treatment area, this is not a limitation on the invention, and preheating of the treatment area is also advantageous when employed with a pulsed radiation source. For such applications, preheating could be achieved by heating the waveguide or the portion of the head in contact with the segment under treatment prior to treatment to heat the skin down to at least to the depth where treatment is desired to a temperature which temperature is below that at which thermal damage occurs; and to then cool the surface in contact with the epidermis to cool the epidermis before irradiation begins. This results in the area under treatment having an elevated temperature when irradiation begins, thereby reducing the energy required from the radiation source.

Alternatively, a low energy radiation source, which can be either the same or different than that used for treatment, can be used to perform the preheating operation.

The foregoing and other objects, features and advantages of the invention will be apparent in the following more particular description of preferred embodiments of the invention as illustrated in the accompanying drawings.

IN THE DRAWINGS

FIGS. 12a and 12b are perspective views of portions of a head illustrating various techniques for scanning a radiation source across an astigmatic radiation delivery channel;

FIG. 13 is a side sectional view of a head suitable for practicing one aspect of the invention in accordance with a tenth embodiment;

DETAILED DESCRIPTION

Figure 1:
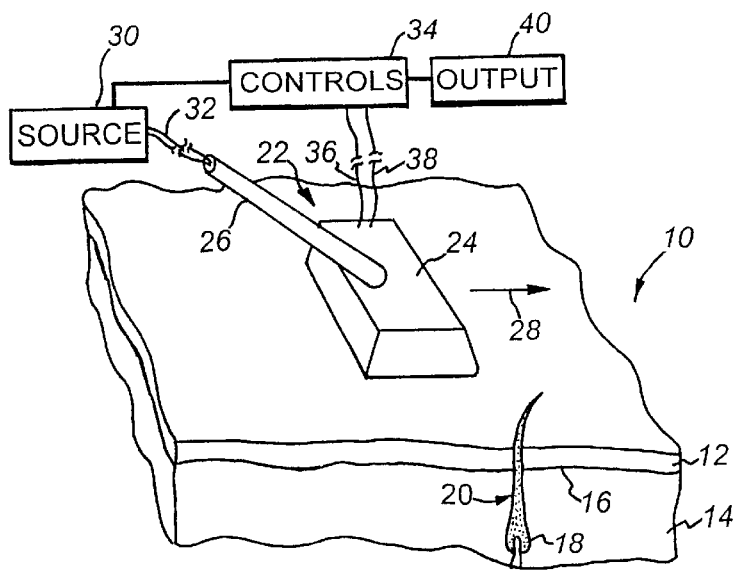
FIG. 1 is a semi-schematic perspective view of apparatus suitable for practicing the teachings of this invention.

FIG. 1 illustrates a general system suitable for practicing the teachings of this invention. In FIG. 1, an area 10 of a patient's skin is shown on which a selected dermatologic treatment is to be performed. As indicated earlier, the treatment may be for removal of unwanted hair, tattoos, port wine stains, spider veins or other vascular lesions, etc. The patient's skin has an epidermal layer 12 and a dermal layer 14, with a dermal-epidermal (D/E) junction or basal layer 16 therebetween. While some dermatologic treatments may involve heating the epidermis 17, such as for example skin resurfacing, most dermatologic treatments which involve the use of optical radiation treat a condition located at a selected volume (sometimes hereinafter referred to as the target volume or target) within dermal layer 14. For example, when the dermatological treatment is hair removal, it may be desired to heat and destroy the bulb 18 of a hair follicle 20. While epidermis 12 might for example be 0.01 cm deep, bulb 18 might, for example, be 3.0 to 5.0 millimeters into the skin. Utilizing the teachings of this invention, a plurality of hair follicles 20 may be simultaneously heated and destroyed.

The apparatus of this invention includes an applicator 22 which may be mechanically driven, but which, for purposes of the following discussion, will be assumed to be hand operated (i.e., translated over the skin surface by hand). Applicator 22 includes a head 24 in contact with the patient's skin in the treatment area and a handle 26 which may be grasped by an operator to move head 24 in for example direction 28 across the patient's skin while preferably maintaining contact between head 24 and the patient's skin. Such contact should be under sufficient pressure between the surface of the head and the skin surface so as to, for preferred embodiments, assure good thermal and optical contact therebetween. Such pressure can be achieved by pressing the head against the skin, by using negative pressure to press the skin against the head or some combination of the two.

For some embodiments of the invention, a source of optical radiation 30 is connected to a light pipe 32, which for the embodiment of FIG. 1 is shown as extending through handle 26, but may otherwise be connected to head 24, to selectively provide optical radiation to the head, radiation being applied through the head, in a manner to be discussed later, to the patient's skin. Source 30 may be a coherent light source such as a ruby, alexandrite, or other solid laser source, a gaseous laser source, or a diode laser source, or may be an incoherent light source such as a flashlamp, fluorescent lamp, halogen lamp, or other suitable lamp. Depending on the desired treatment, the radiant energy may be at a single wavelength, with incoherent light sources being filtered to provide the desired wavelength, or over a selected band of wavelengths. In the following discussion, when it is indicated that radiation is being applied at a selected wavelength, this will mean either a single wavelength or a wavelength band, as appropriate. Source 30 in accordance with preferred embodiments of this invention is also a CW source which, for purposes of this invention shall be defined as either a light source which is producing radiation continuously or a pulsed source with a high repetition rate/frequency, and in particular which has a delay between pulses which is less than the dwell time of the head on a given segment. CW radiation is defined as radiation from either such source.

While in FIG. 1 source 30 is shown as external to head 24, for some embodiments of the invention which involve the use of a diode laser, diode laser bar or other sufficiently compact radiation source, the source may be located in head 24, with wires for controlling and energizing the source being connected through handle 26 or otherwise to the head.

Controls 34 are also provided which receive certain information from head 24 over lines 36, for example information relating to rate of movement of head 24 over the patient's skin, or temperature of the epidermis and which may send control signals to the head over lines 38 as required. Lines 36 and 38 may be part of a cable which is also connected to head 24 through handle 26 or may be otherwise connected to the head. Controls 34 may also generate outputs to control the operation of source 30 and may receive information from the source. Controls 34 may also control selected output devices 40, for example a buzzer, light, vibrator or other feedback control to an operator or, depending on application, may be of other types known in the art.

Figure 2:
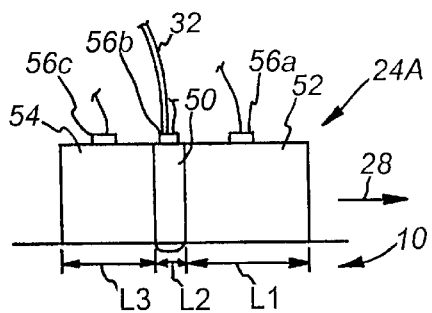
FIG. 2 is a sectional view of a head useful for practicing the teachings of this invention in accordance with a first embodiment.

Before discussing specific embodiments for head 24 and the manner in which the system of FIG. 1 may be utilized to treat various dermatological conditions in accordance with such embodiments, it should be appreciated that maintaining head 24 in good thermal and optical contact with the surface of the patient's skin during treatment while applying CW radiation from source 30, whether located external to head 24 as shown in FIG. 1 or within the head, offers a number of significant advantages when performing various dermatological treatments. First, as indicated earlier, for the same radiation source operating at comparable energy levels, a CW source is almost always substantially less expensive than a comparable pulsed source. Therefore, the ability to use a CW source results in a significant reduction in system cost. Second, if head 24 is moved across the surface of the patient's skin at a substantially uniform rate, the radiation applied to the patient's skin at each point along the path of travel of head 24 is substantially the same, something which, as indicated above, cannot easily be achieved with a pulsed radiation source. The head being in good optical contact with the patient's skin improves the efficiencies of energy transfer into the skin, further reducing the size and cost of the required energy source. Further, the head 24 being in good thermal contact with the patient's skin permits the head to be used to heat the volume in the patient's dermis at which treatment is to occur, for example the area of bulb 18 for a hair removal procedure, so as to reduce the amount of energy required from the radiation source in order to perform the desired procedure at this volume, thus further reducing the cost of such source. Good thermal contact also permits the head to be utilized to cool the patient's epidermis 12 before irradiation, during irradiation, and after irradiation, to protect the epidermis from thermal damage. Applying pressure to head 24 as it is moved across the surface of treatment area 10 also stretches the skin in the treatment area which can provide a number of advantages, including reducing the physical distance between the head and the target volume, reducing the coefficient of scattering in the skin so that more of the applied radiation reaches the target volume and, for hair removal, flattening the hair follicle so as to increase the area of the follicle exposed to radiation. All of these effects reduce the amount of radiation required from the source, thereby further reducing the cost of the system. Various techniques are available for measuring/detecting good thermal contact between a head and the patient's skin including the temperature profile detecting technique of copending application Ser. No. 60/077,726 filed Mar. 12, 1998, which application is incorporated herein by reference. FIG. 2 illustrates one exemplary embodiment for a hand piece 24A suitable for use in practicing the teachings of this invention. In the discussion of this embodiment, and in the embodiments to follow, the same reference numerals will be used for common elements. Letter suffixes will be used for elements which are substantially the same, but differ in some particulars. Thus, the letters 24A, 24B, etc. are used for the various embodiments of handpiece 24.

Handpiece 24A has three sections, an optical channel 50 which is shown in FIG. 2 as a waveguide, a leading section 52 which passes over treatment area 10 before waveguide 50 and a trailing section 54 which passes over the treatment area after waveguide 50. Optical radiation is applied to waveguide 50 through optical fibers 32 (or fiber bundle) or other suitable optical transmission components or, as will be discussed later, laser diodes or other suitable components may be in contact with waveguide 50. Waveguide 50 may also be replaced with a lens or other suitable focusing or non-focusing optical transmission component (a waveguide, lens or other suitable focusing or non-focusing optical transmission component sometimes being collectively referred to hereinafter as an "optical channel"), which optical transmission component receives radiation from the radiation source utilized through a suitable optical transmission path. Other arrangements for getting radiation to optical channel 50 can also be employed.

Sections 52 and 54 are each formed of a metal or other material having good thermal conduction properties. Sections 52 and 54 may be formed as a single block of a single material, with optical channel 50 being formed in the block, or, where sections 52 and 54 are to have different temperature profiles, the sections may, as will be discussed later, be two separate sections of the same or different materials secured together with a layer of thermal insulation therebetween. In FIG. 2, a thermal component 56a, 56b, 56c is shown in contact with section 52, waveguide 50, and section 54, respectively. For a preferred embodiment, each of the thermal components 56 is a thermoelectric element such as a Peltier effect device; however, other mechanisms for controlling temperature known in the art, including flowing water, and flowing gas or spray at a desired temperature may be utilized for thermal components 56. In applications where sections 52 and 54 have the same temperature profile, the same thermal component may be used to control the temperature of both sections; however, particularly if thermoelectric components are used, it is preferable that a number of these components be utilized, distributed over sections 52 and 54 so as to achieve a substantially uniform temperature distribution in these sections.

Figure 3:
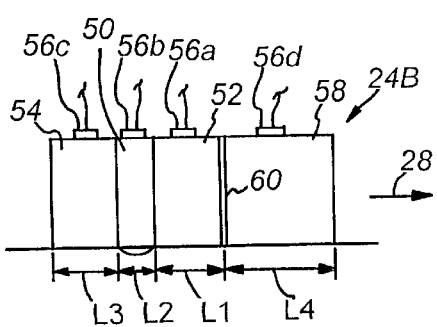
FIG. 3 is a sectional view of a head suitable for practicing the teachings of this invention in accordance with a second embodiment.

FIG. 3 shows a head 24B which is substantially the same as the head 24A shown in FIG. 2 except that, in addition to sections 52 and 54, head 24B also has a section 58, ahead of section 52, with a thermal insulation layer 60 being provided between sections 52 and 58. Section 58 is also formed of a metal or other material having good thermal conduction characteristics and a thermal element 56d, for example one or more thermoelectric or thermal resistance elements, is provided in thermal contact with section 58. As will be discussed shortly, section 58 is intended to have a different temperature profile than section 52.

For the embodiment of FIG. 2, section 52 may be utilized to either pre-heat or pre-cool the patient's skin in the treatment area. For a head 24 moving at a velocity V in direction 28, V sometimes also being referred to as the "scanning velocity", and for a length of section 52 in the direction of movement 28 equal to $L_1$, the time $T_1$ during which section 52 is over a segment of the patient's skin prior to treatment, and thus the time of pre-heating or pre-cooling, is roughly $$T_1 = \frac{L_1}{V}$$

directly proportional to $L_1$ and inversely proportional to V. Thus, $$T_z = \frac{z^2}{4\alpha}$$

Since the time it takes for a temperature wave to penetrate to a depth z in the skin is, where $\alpha$ is the skin thermal-diffusion coefficient ($\alpha \approx 1.5 \cdot 10^{-3}$ cm$^2$/s). Therefore if these two times ($T_1$ and $T_z$) are roughly equal, then:

$$z = \frac{\sqrt{4\alpha \cdot L_1}}{V}$$

and the desired thermal effect will reach a desired depth z during the period that section 52 overlies the skin segment. Thus, $L_1$ and V can be selected so as to achieve the desired thermal effect at a desired depth in the skin prior to irradiation. Since, as will be discussed shortly, V is also a factor in determining the duration of irradiation for achieving the desired therapeutic effect, $L_1$ may be the prime factor in determining the depth for the desired thermal effect. For pre-heating, the depth z is the depth of the volume at which treatment is desired. For example, referring to FIG. 1, z might be the depth of bulb 18 of a hair follicle where the treatment is hair 15 removal. For pre-cooling, it is generally desired to cool the entire epidermis 12 to DE junction 16. It is generally undesirable to cool significantly below the DE junction since this may interfere with treatment by having some cooling effect on the treatment or target volume. Depending on the function section 52 is to perform and the scanning rate V, $L_1$ is selected so as to achieve the desired thermal effect to the desired depth z.

FIG. 3 differs from FIG. 2 in that there are two pre-temperature modifying sections 52 and 58. With this arrangement, section 58 is typically heated to pre-heat to the depth $z_C$ of the target volume. Section 52 is cooled and is intended to subsequently cool the epidermis to roughly DE junction 16. Since heating performed by section 58 is to a greater depth than the cooling performed by section 52, $L_4$ is shown as being greater than $L_1$ in FIG. 3. The combination of sections 52 and 58 permits the target to be heated and remain heated prior to irradiation while the epidermis is protected against thermal damage by being cooled prior to irradiation.

The temperature profile at the depth z is a function of the initial temperature of the skin and of the temperature of the section 52, 58 for head 24B. The length of the segment $L_1$ and scanning velocity V are also factors in determining the final temperature at depth z. An estimate $$T(z, V, L_1) = 2 \cdot \frac{T_0 - T_1}{\sqrt{\pi}} \cdot \int_0^{\frac{z}{2\sqrt{\frac{\alpha L_1}{V}}}} e^{-\xi^2} d\xi \_T_1$$

of skin temperature at depth z can be made using Thomson's equation as follows:
where $T_0$ is the initial temperature of the skin, $T_1$ is the initial temperature of the segment which is assumed for purposes of the equation to be segment 52. For scanning velocities in the range of approximately 0.05 to 10 cm/s, and length L of approximately 0.125 cm, desired pre-heating to a temperature in the range of +40° C. to +60° C. or pre-cooling of −30° C. to +20° C. can be achieved. Typically, the epidermis would be cooled to the DE junction to a temperature in the −5° C. to 0° C. range. Scanning velocities up to 10 cm/s should be achievable with contact scanning, but scanning velocities in excess of 10 cm/s may be more difficult to achieve.

The embodiment of FIG. 3 complicates the determination of appropriate parameters since scanning velocity V, which is the same for all sections, must be selected so that pre-heating can be achieved to a desired depth with an $L_4$ of reasonable size, pre-cooling to the DE junction can be achieved with an $L_1$ of reasonable size, and the desired therapeutic effect can be achieved, using the radiation source with a given fluence and for a reasonably achievable value of $L_2$. This is somewhat complicated by the fact that in order to heat deep layers of the skin (i.e., greater than 3 mm) the scanning velocity should not exceed approximately 0.1 to 0.2 cm/s, while for heating of subsurface layers of the skin (less than 1 mm) the scanning velocity can be up to 2 cm/s. This assumes an $L_4$ of approximately 5 cm or less.

Radiation passing through waveguide or other optically transparent component 50 is directed through the epidermis, which has preferably been pre-cooled to the target, which may have been pre-heated, in order to achieve the desired therapeutic effect. In determining the time during which the target is irradiated, account must be taken of the fact that, due to scattering in the patient's skin, the beam width at the target can be greater than $L_2$, the width of radiation at the skin surface, by a value $\Delta$. Value $L_2+\Delta$ can be minimized by focusing of the beam. Thus, $$T_2 = \frac{L_2 + \Delta}{V}$$

the exposure time $T_2$ of the target to CW radiation is given as,

The target has a thermal relaxation time which is generally a function of its size and of its shape. It is generally desirable that the time $T_2$ be roughly equal to the thermal relaxation time of the target, assuming destruction of the target is the desired therapeutic effect, since this results in maximum heating of the target with minimal heating of surrounding tissue. In applications such as hair removal, where it has been found that some damage to a small layer of tissue surrounding the follicle facilitates permanent, or at least more permanent, hair removal, it may be desirable for the time $T_2$ to be slightly greater than the thermal relaxation time of the target. In any event, for a target having a size or diameter d, the critical velocity at which dwell time on the target is $$V_c = \frac{g(L_2 + \Delta)\alpha}{d^2}$$

roughly equal to its thermal relaxation time is given by,
where g is shape factor (g=8, 16 and 24 for stratified, cylindrical and spherical targets, respectively). Thus, where bulb 18 of a follicle is the target, g would be approximately 24. Assuming a maximum scanning velocity of 10 cm/s, and also assuming a depth z≈3 mm and $L_2+\Delta$ of about 3 mm, equation (6) suggests that the process works best for stratified targets like fat layer with a thickness greater than 190 µm, cylindrical targets like a blood vessel with a diameter greater than 270 μm, and spherical targets like a hair bulb with a diameter greater than 320 μm. However, since, as discussed earlier, lower velocities would typically be employed in order to achieve pre-heating and/or pre-cooling for section 52, 58, significantly larger minimum target volumes are required for the various shapes in a practical system. However, since $V_C$ is only a guide, and times less than or greater than thermal relaxation time of the target may be appropriate in some treatments, treatable target sizes will also vary. Effective pre-heating of the target may also reduce the required dwell time to achieve a desired therapeutic effect.

Another concern when employing the teachings of this invention for dermatologic treatment is that the temperature rise at the target be sufficient to achieve the desired effect. Where the treatment being performed is hair removal utilizing techniques similar to those described in U.S. Pat. No. 5,735,844 issued Apr. 7, 1998, it is necessary to heat the hair bulb to a temperature of approximately 65° C. to 75° C. The maximum temperature of a hair bulb $$T_m = \frac{6\tau(d)\left(1 - \exp\left(-\frac{a}{\tau(d) \cdot V}\right)\right)}{c \cdot \rho \cdot d} k(\lambda) \cdot \psi(z, \lambda) \cdot P + T_0$$

undergoing irradiation is given by the following equation, where, z is the depth of the bulb 18 in the skin $T_0$ is the initial temperature of the bulb before irradiation a is the size of the irradiate zone inside the skin along the scanning direction at the depth z (as previously indicated a=$L_2$+Δ)

c and p are the heat-capacity and density of the bulb respectively k(λ) is the absorbing ability of the hair bulb and shaft defined by a concentration and a type of melanin, and depends on wavelength (is greater for dark hair and less for lighter hair)

ψ(z, λ) is the radiance inside the skin at the depth z, caused by a light flux of unit power per length. It depends on both scattering and absorption inside the skin P is the power per unit length (i.e., equal to the total power applied to the skin surface per width of the light beam in the direction perpendicular to the direction of scanning. P is in units of W/cm.

$\tau(d)=d^2/g\alpha$ is a period of thermal relaxation, where d is a diameter of the bulb, g is as previously indicated equal to 24 for a hair bulb, and α is the thermal diffusion coefficient of the tissue around the bulb.

For the destruction of a hair bulb, λ is in a range of 600–1200 nm and is preferably in a range of 670–1100 nm. In this range, k(λ) varies from 1–0.1 and decreases with increasing wavelength. ψ(z, λ) in this range increases with wavelength because of the weakening of the skin scattering properties and decreases with depth. At a depth of 3–5 mm where a hair bulb in its anagen stage is typically locate, this value, which is sometimes referred to as radiance attenuation, is in the range of 0.1–0.5. This value may be significantly increased where focusing techniques to be described later are used. With focusing, the reflection coefficient of light from the skin can be 20%–70%. Further, reflection of light scattered from the skin back into it by various means to be described increases the radiance in the zone of the hair bulge or in a hair bulb 1.2–2.5 times. Thus, the devices of this invention can allow ψ(z, λ) to be increased to 0.5–1.

Figure 15:
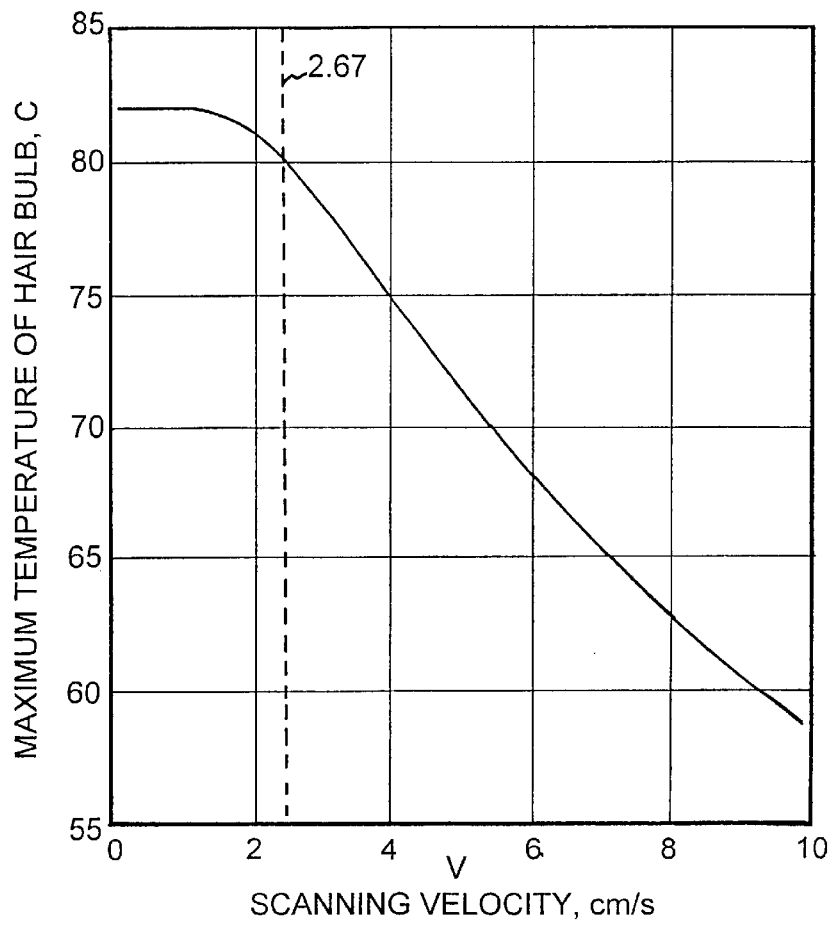
FIG. 15 is a chart illustrating the relationship between scanning velocity of the head and the maximum temperature of a hair bulb located at a selected depth.

From the above, it can be seen that, once the geometry of the systems has been selected, the temperature at the bulb is directly proportional to the applied power P and is inversely proportional to the velocity V in a more complex way. FIG. 15 illustrates the dependence of $$T_m = \frac{6 \cdot P \cdot d \cdot k \cdot \psi}{g \cdot \alpha \cdot c \cdot \rho \cdot a} + T_0$$

maximum temperature at a hair bulb on scanning velocity V for typical parameters. The curve of FIG. 15 is calculated assuming a=0.3 cm, k=0.5, ψ=0.5, P=40 W/cm², d=0.03 cm. From FIG. 15, it is seen that at low scanning velocities, $T_m$ does not depend on scanning velocity and is equal to $$V_m = \frac{g \cdot a \cdot \alpha}{3 \cdot d^2}$$

When the scanning velocity exceeds temperature $T_m$ starts to decrease.

Figure 16:
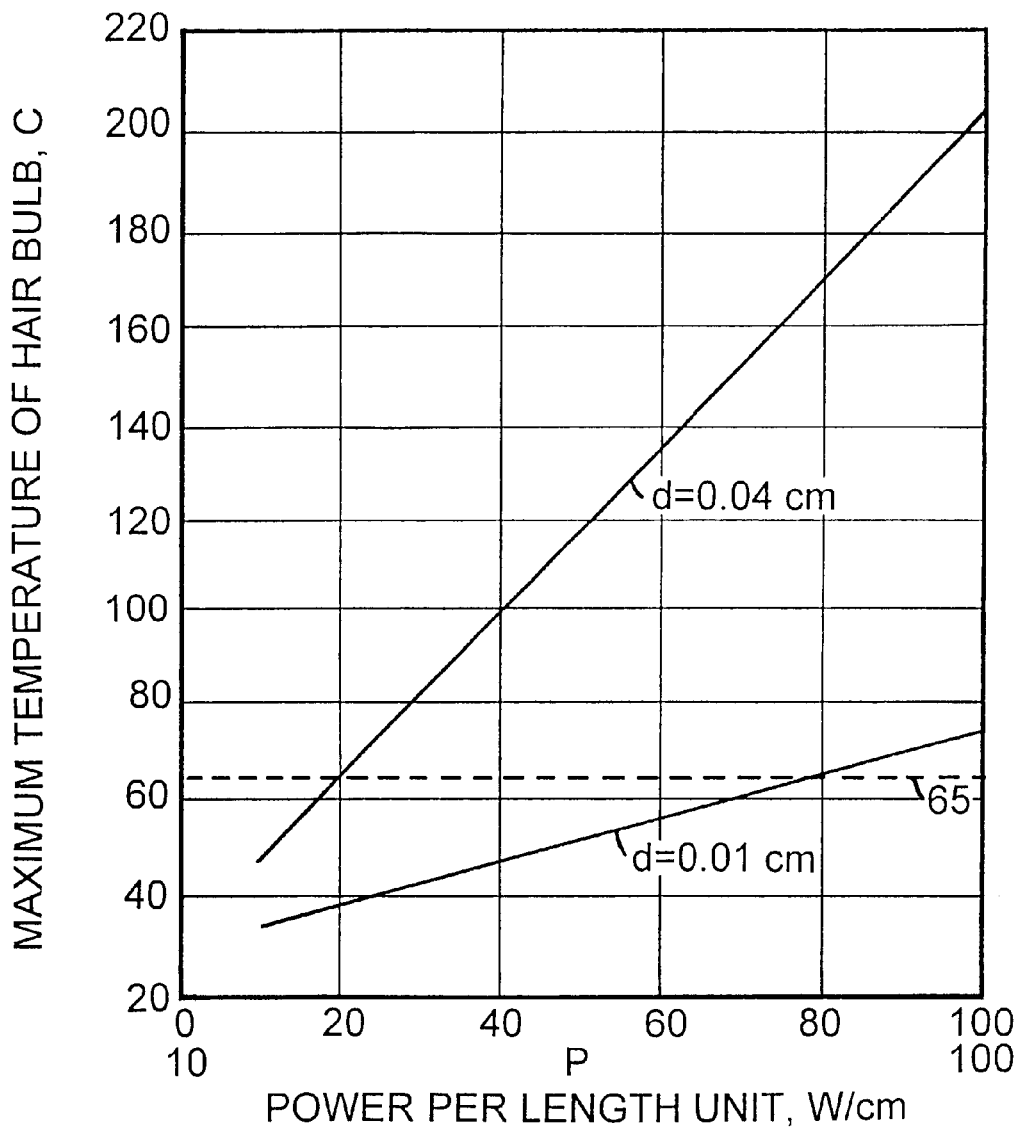
FIG. 16 is a chart illustrating the relationship between power per unit length and maximum temperature of the hair bulb at a selected depth for two different sizes of hair bulb.

When V is less than $V_m$, the average temperature of the hair bulb does not change with changing velocity, but selectivity of thermal damage decreases. Thus, by decreasing the velocity of scanning, it is possible to increase the diameter of the zone of thermal damage around the hair bulb. Maximum scanning velocity depends on the hair bulb dimension and decreases as the size of the follicle increases. FIG. 16 shows the dependence of $T_m$ for a hair bulb on the power per unit length P. For a treatment period of less than 1 second, denaturization of protein structures is observed at temperature exceeding 65° C. From FIG. 16, it is seen that maximum temperature $T_m$ at a hair bulb is also a function of the power P per unit length. For a treatment of less than 1 second, denaturization of protein structures is observed to occur at temperatures exceeding 65° C. FIG. 16 also illustrates that the power required to cause thermal damage in a hair bulb is inversely proportional to the size of the hair bulb (i.e., thermal damage is caused at a lower power for a large bulb than for a small bulb).

Thus, for hair removal, and regardless of the embodiment utilized, the following parameters would apply:

1. Wavelength: 600–1200 nm;
2. average power per length unit: 5–150 W/cm;
3. width of beam along direction of scanning: 0.05–5 mm;
4. scanning velocity: 0.01–10 cm/s;
5. temperature of cooling: −20° C.–+30° C.

For preferred embodiments, optically transparent section 50 is also cooled by thermal element(s) 56b so as to prevent, or at least limit, heating of epidermis 12 in the treatment area during irradiation. This cooling effect is also a function of the scanning velocity and is particularly critical where irradiation used is of a wavelength which preferentially targets melanin, as is for example the case for certain hair removal treatments. Since there is a high concentration of melanin at DE junction 16, it is desirable that V be slow enough so as to permit heat produced at the DE junction to be removed through the cooled waveguide or other cooled optically transparent element 50. The maximum scanning velocity at which the cooling effect $$V_{max} = \frac{4 \cdot L_2 \cdot \alpha}{z^2}$$

becomes noticeable for a given depth z is given by,

Where epidermis 12 to be cooled has a thickness of approximately 100 µm and the length $L_2$ is approximately 1 mm, $V_{max}$=6 cm/s.

Further, as indicated earlier, the pressure applied to the skin by head 24 in general, and by the skin-contacting surface of element 50 in particular, has a number of advantages, including improving the optical transmission (i.e., reducing scattering) for radiation passing through the skin. The head moving in the direction 28 over area 10 of the skin also stretches the skin in the direction of scanning resulting in an additional increase in skin transmission and thus the depth of electromagnetic wave penetration into the skin. Further, when the target is for example a hair follicle, the stretching of the skin turns the follicle to cause the radiation to impinge on a larger portion of the follicle and brings the follicle nearer to the skin surface.

Section 54 continues to cool the epidermis after irradiation to further guard against potential thermal damage to the skin. Unlike lengths $L_1$, $L_2$ and $L_4$ which are fairly critical, the length $L_3$ is not critical. The purpose of this section is to assure that the epidermis is not overheated and, if the prior sections are effective in keeping the epidermis temperature down, section 54 may not be required.

Figure 6:
FIGS. 6a–6b illustrate two embodiments of astigmatic transparent channel suitable for use in a head of the various embodiments to deliver radiant energy.
Figure 6:
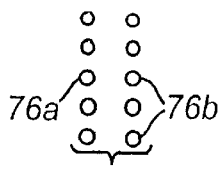

Since it is generally desirable to decrease the time element 50 is over the target, it is generally desirable that $L_2$ be kept small. However, in order to achieve more rapid treatment, a significant beam aperture is desirable. This suggests that the dimension of the beam perpendicular to the direction of movement should be relatively large, resulting in an aperture for the skin contacting surface of element 50 which has an astigmatic shape, which shape may also be asymmetric. FIG. 6 illustrates two such shapes, namely an oval 66 (FIG. 6a), and a series of adjacent light pipes 76a, 76b as shown in FIG. 6b, the light pipes of FIG. 6b being discussed in greater detail in conjunction with FIG. 4. These shapes are just examples of astigmatic shapes for an optical aperture, and many other astigmatic shapes are within the contemplation of the invention.

Figure 9:
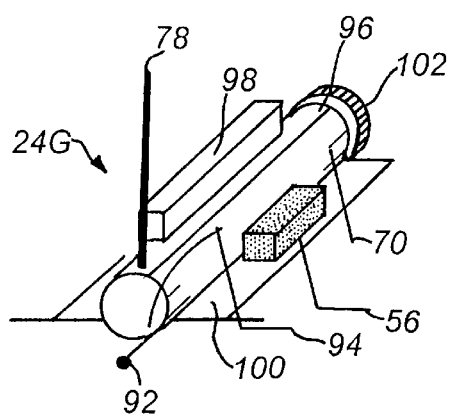
FIG. 9 is a top perspective view of a head suitable for practicing the teachings of this invention in accordance with a seventh embodiment.

Further, in order to deliver the radiation to a significant depth (i.e., greater than 1 mm) efficiently, large diameter beams are generally required to overcome the effect of scattering. With astigmatic beams of the type shown in FIG. 6, it is therefore desirable that focusing of the beam in a direction perpendicular to the direction of scanning be used. One way of achieving this is through use of a cylindrical lens 70 such as is shown in FIG. 9 which lens has a small radius of curvature (for example less than 10 mm). However, such focusing can perhaps be better achieved through use of a head 24C such as that shown in FIG. 4. This head has a section 52 which functions in the same way as section 52 of head 24A to pre-cool or pre-heat the area under treatment. Section 52 is separated from a section 72 of the head by a layer of thermal insulation material 74. Section 72 is also formed of a metal or other material having good thermal conduction properties. Two rows of micro-optic elements 76a and 76b are provided which extend through section 72 and are angled so that their focuses are combined along a common line located at the target depth. Microlenses may be included at the distal ends of elements 76 to enhance focusing. This technique allows the beams to be targeted into the skin at angles greater and can be achieved using optical systems and more effectively compensates for the scattering of radiation in the skin. Section 72 would be cooled, preferably by a number of thermoelectrical elements 56b, so as to provide both pre-cooling of the epidermis prior to irradiation, cooling of the epidermis during irradiation, and post-cooling of the epidermis. Section 72 can thus perform the cooling functions of sections 50, 52 and 54 of for example the embodiment of FIG. 2. Thus, for this embodiment of the invention, section 52 can be used as a pre-heater or can be eliminated.

Figure 4:
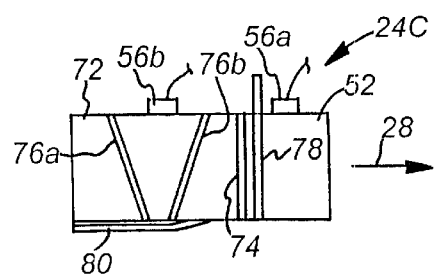
FIG. 4 is a sectional view of a head suitable for practicing the teachings of this invention in accordance with a third embodiment.

FIG. 4 also illustrates some additional features. First, it shows an optical channel 78 which can be connected to a suitable detector in controls 34 for detecting the scan velocity of head 28. Other techniques which will be discussed in conjunction with FIG. 10 may also be used for performing this function. Detecting scan velocity permits controls 35 to operate output 40 if the scan velocity is detected to be outside of desired ranges so as to alert the operator so that the rate may be increased or decreased as appropriate. For example, the output may be a red or a green light on some portion of applicator 22 or a console associated therewith, might be a voice, or buzzer or other audio alert to the operator, might be a vibrator in the handle 26, or might be some other appropriate warning to the operator. In the event the rate is detected as being so slow (or even no movement at all) as to present a potential danger of injury to the patient, controls 34 might also deactivate source 30 so as to protect the patient.

One problem with radiation treatments is that a significant percentage of the radiation applied to the skin is reflected back or backscattered by the skin and lost. Various schemes have been proposed in the past for retroreflecting such radiation back into the skin, including for example putting some type of reflector in section 50. Sections 52 and 54 might also have a reflective coating on their skin contacting surfaces to reflect such radiation back into the skin. Section 72 is particularly useful for this purpose since the entire skin-contacting surface 80 of this section may be formed of highly reflective material, or have a highly reflective coating formed thereon. By redirecting most of the radiation back into the skin, the intensity of radiation inside the skin can be increased 1.2 to 2.5 times.

Figure 5:
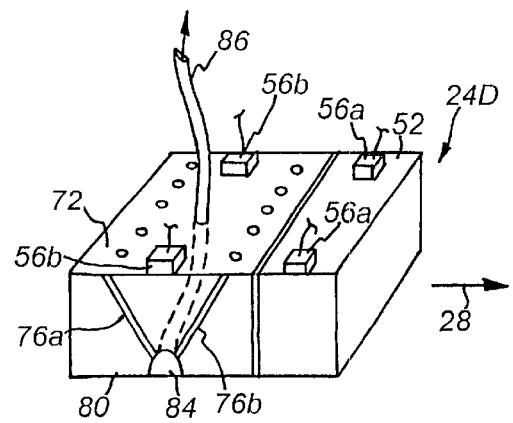
FIG. 5 is a perspective sectional view of a head suitable for practicing the teachings of this invention in accordance with a fourth embodiment.

FIG. 5 shows a head 24D an embodiment of the invention which differs from that shown in FIG. 4 only in that there is a recessed channel 84 formed in skin-contacting surface 80 of section 72, and that optical channels 76a and 76b terminate on opposite sides of channel 84, with their focal point being at a point in the recess, for example at the substantial center thereof. A hose 86 is connected at one end to the top of channel 84 and at the other end to a source of negative pressure. As head 24D moves in direction 28 across the patient's skin, folds of the patient's skin are drawn into channel 84. The size of channel 84 is selected such that the target is included in the fold of skin drawn into channel 84 and is irradiated from both sides by radiation applied to optical channels 76. For example, if head 24D is being used for hair removal, channel 84 might be 1 to 6 millimeters wide and 1 to 6 millimeters deep, a size which would generally result in the fold having only a single hair follicle in the plane shown in the figure, although multiple hair follicles may be in the channel along its long dimension. The configuration of FIG. 5 has several advantages. First, it reduces the distance for radiation to reach the target and more effectively focuses radiation on the target. Second, if the channel is formed of an optically reflective material, the walls of channel 84 reflect substantially all of the radiation leaving the skin back into the fold, providing for very efficient irradiation.

Figure 7:
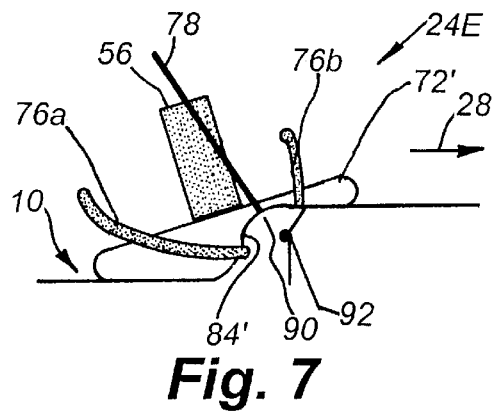
FIG. 7 is a side view of a head in use which is suitable for practicing the teachings of this invention in accordance with a fifth embodiment.

While in FIG. 5 it is assumed that a line connected to a vacuum or other source of negative pressure is utilized to draw a fold of skin into channel 84, a bellows or other suitable mechanism could also be utilized for drawing the skin into channel 84 or, as shown in FIG. 7, a head 24E could be provided having a channel 84' formed in a body 72' of a thermal conductive material, which channel is shaped so that a fold of skin 90 which includes the target 92 is forced into channel 84' as head 24E is moved in direction 28 over the patient's skin. Successive folds of the patient's skin would be pushed into channel 84' as the head moves so as to provide substantially uniform irradiation of the skin in treatment area 10. Except that a pre-heater section 52 is not included, the embodiment of FIG. 7 would otherwise operate in substantially the same way as in the embodiment of FIG. 5 and would afford substantially the same advantages.

Figure 8:
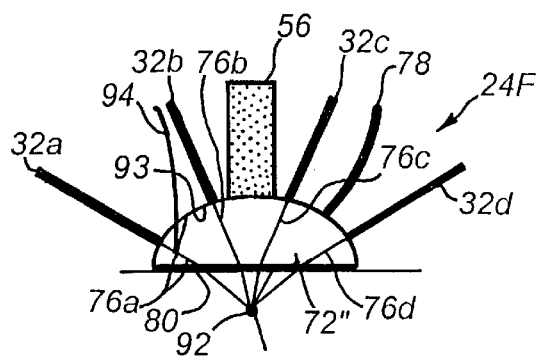
FIG. 8 is a side sectional view of a head suitable for practicing the teachings of this invention in accordance with a sixth embodiment.

FIG. 8 shows a head 24F which differs from those previously described in that it has four sets of optical channels 76, channel 76a, 76b, 76c, and 76d, which for this embodiment are merely light paths through a transparent block or air, each of which is fed by a corresponding flexible waveguides 32a–32d, respectively. All of the optical channels 76 are angled so as to be substantially focused at target depth 92. Body 72" is curved to facilitate the placement of channels 76 and also has a reflecting top surface 93. In addition to components previously mentioned, FIG. 8 also includes a line 94 leading from a thermocouple or other suitable temperature sensor mounted close to surface 80 or in surface 80. Temperature sensor line 94 connects to controls 34 and may be utilized to control epidermal temperatures or for other suitable purposes.

FIG. 9 shows still another embodiment of the invention which, as previously indicated, utilizes a cylindrical lens 70 having a transparent window 96 against which is mounted a radiation source 98, which may for example be a laser diode bar, a lamp with a reflector, or other radiation source which is small enough to be mounted in the handpiece. A reflection plate 100 is provided to perform the retroreflection function for back scattering light. FIG. 9 also shows a kinematic motion sensor 102 which may either supplement optical motion sensor 73 or may be used in lieu thereof. Kinematic motion sensor 102 may for example be a wheel which turns as cylindrical lens 70 is moved over the skin surface to provide a signal to controls 34 indicative of scan velocity. Temperature control element 56 is shown as being in contact with both lens 70 and reflection plate 100 so as to cool both elements, thereby providing both pre-cooling of the treatment area and cooling during irradiation. There is preferably a second element 56 on the opposite side of cylinder 70 in contact with plate 100 on the trailing side of the lens which is operative both to further cool the lens and to cool reflection plate 100 and the portion thereof trailing the lens to provide post-cooling. As indicated previously, cylindrical lens 70, particularly if it has a relatively small diameter, for example of less than 20 mm, is also operative to focus the radiation at target 92 and partly compensate the scattering effect of skin. Except as indicated above, the embodiment of FIG. 9 operates substantially the same as the prior embodiments to provide scanned CW dermatologic treatment. It should also be noted that, while FIG. 9 is the only embodiment showing the radiation source 98 located in head 24 as opposed to the radiation being applied to the head from an external source 30 through optical leads 32, an external source 30 or an internal source 98 for the head is interchangeable for all embodiments, so that any of the prior embodiments may have an internal radiation source 98 in lieu of the arrangement shown, and the embodiment of FIG. 9 may have an external radiation source with optical leads 32 impinging on transparent window 96. For an embodiment such as that shown in FIG. 8, a separate laser diode bar or bars 98 might for example be provided for each of the optical channels 76a–76d.

Figure 10:
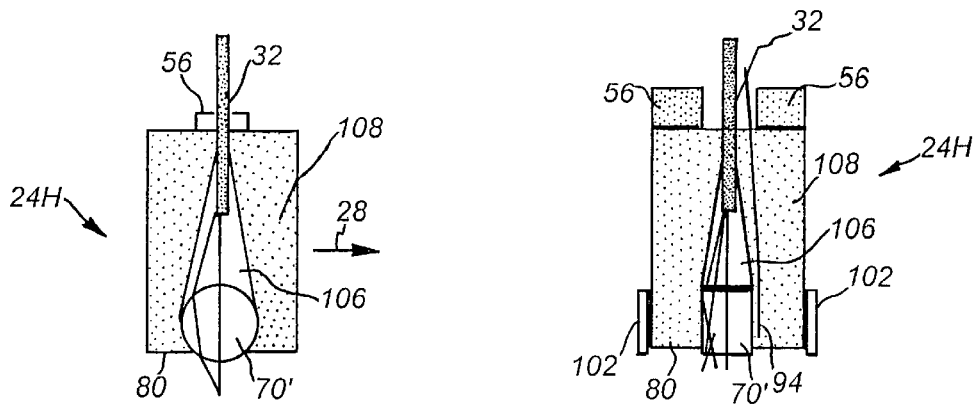
FIGS. 10a and 10b are a side sectional view and a front view, respectively, of a head suitable for practicing the teachings of this invention in accordance with an eighth embodiment.

FIGS. 10A and 10B show still another handpiece 24H suitable for practicing the teachings of the invention. This handpiece differs from those previously shown in that rather than radiant energy being applied directly to the optical waveguide, lens or other transparent component through which radiant energy is applied to the patient's skin, optical lines 32 terminate in a cavity 106 formed in a body 108 of copper or of some other material having good thermal conduction properties. The walls of chamber 106 are polished, coated or otherwise treated to have highly reflective, and preferably totally reflective, surfaces. The advantage of the configuration shown in FIG. 10 with chamber 106 is that radiant energy enters cylindrical lens or astigmatic microobjective 70' at a variety of angles which can be focused by the lens/microobjective to the desired depth in the skin, the focusing action being more efficient when the light enters the lens at a variety of angles than at a single angle. Cylindrical lens 70' may be mounted in body 108 either rigidly, as for the embodiment of FIG. 9, or may be mounted for rotation in the body. Rotation of the lens facilitates movement of the head over the patient's skin, but prevents the desired stretching of the skin. However, a rotating lens is within the contemplation of the invention. Thermal elements 56 cool body 102, resulting in both pre-heating, cooling and post-cooling of the epidermis and also resulting in the cooling of cylindrical lens 70' which cools the epidermis during irradiation. Body 108 a has reflective skin-contacting surfaces 80 to retroreflect back scattering light from the patient's skin. Fig. 10 also illustrates kinematic motion sensor 102 and a thermocouple or other suitable temperature sensor 94. Except for the differences discussed above, the embodiment of FIG. 10 functions substantially the same as the embodiments previously discussed.

Figure 11:
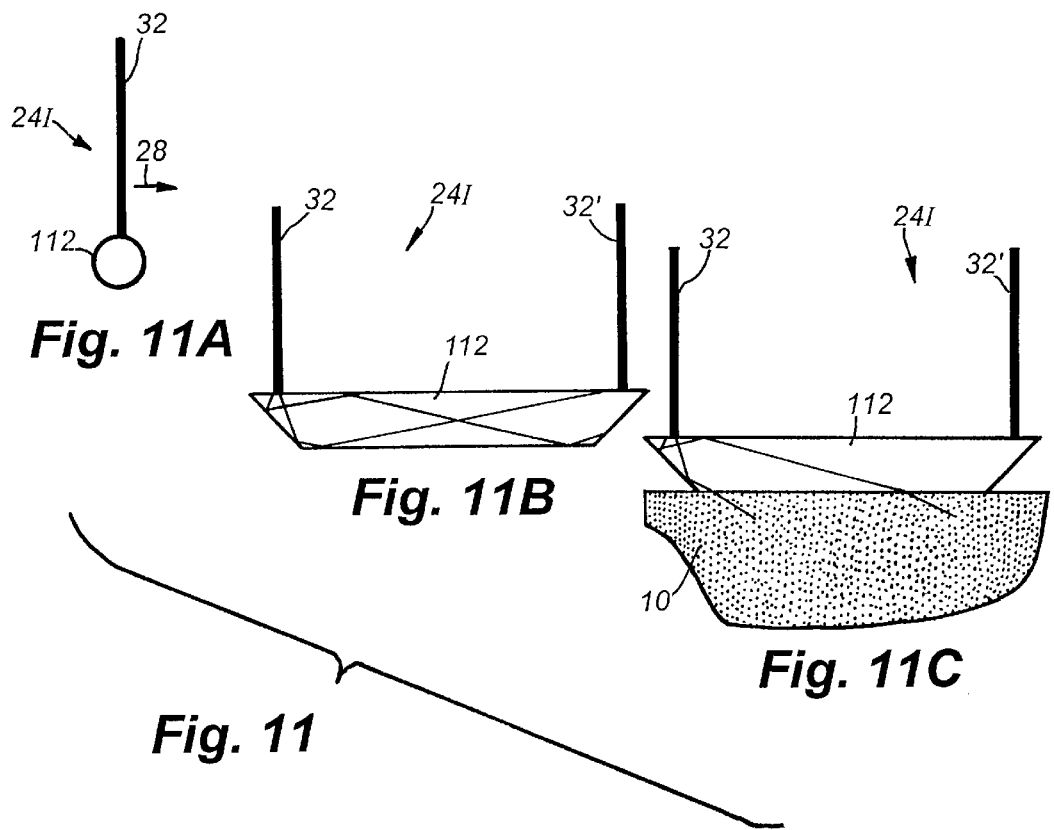
FIGS. 11a, 11b and 11c are a side view, a front view when not in contact with a patient's skin, and a front view in contact with the patient's skin, for a head suitable for practicing the teachings of this invention in accordance with a ninth embodiment.
Figure 14:
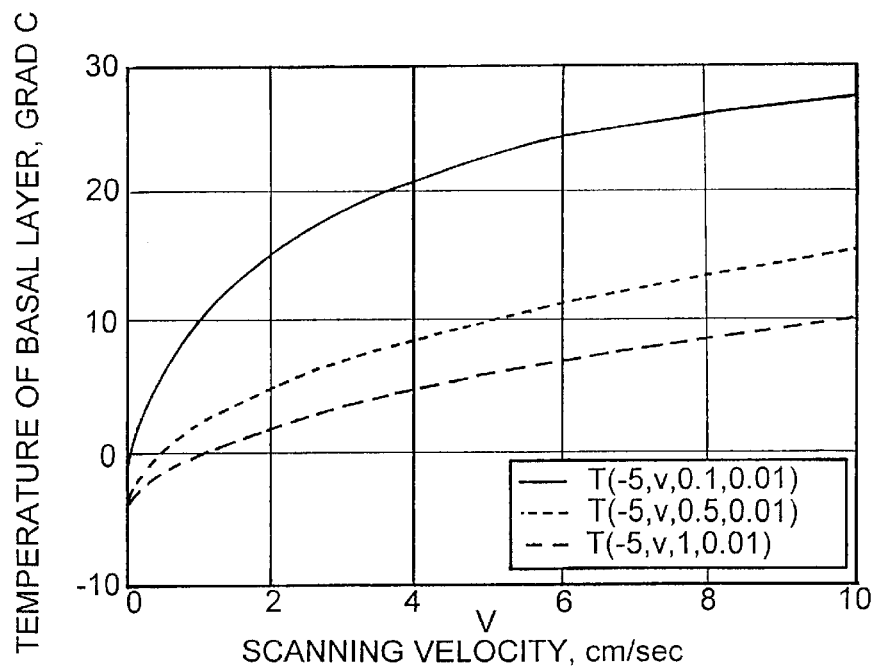
FIG. 14 is a graph illustrating the relationship between temperature at the basal layer and scanning velocity when practicing the teachings of this invention.

FIGS. 11a–11c illustrate still another embodiment 24I for the head. With this embodiment, cylindrical lens 112, which for example is formed of sapphire, is treated to normally have total internal reflection so that light or other radiation entering the lens through optical line 32 is reflected through the lens and exits through optical lines 32'. However, when lens 112 is in contact with the patient's skin as shown in FIG. 11c, the total internal reflection at the skin-contacting surface is broken due to the change of index of refraction at this surface so that light energy is emitted from the lens into the patient's skin. The use of the total internal reflection lens 112 of FIG. 11 is a safety feature which assures that radiation is not applied to a patient or other person unless handpiece 24 is in contact with a patient's skin in the area to be treated. Except for this difference, the embodiment of FIG. 11 functions in the manner described for previous embodiments and components such as a housing for pre- and post-cooling, a chiller for the lens, motion sensors, etc. of prior embodiments might also be used with this embodiment.

While for the embodiments of the invention described so far radiation energy is applied in parallel along the length of the head during irradiation, FIGS. 12a and 12b illustrate embodiments of the invention where light is rapidly scanned. In FIG. 12a, radiant energy applied to the head over a line 32 impinges on a deflector 120 which is oscillated at a rate such that the impinging radiation is scanned in the direction indicated by arrows 122 at the rate previously indicated across a cylindrical lens 70". In FIG. 12b, the impinging radiation 32 is also applied to an oscillating deflector 120 which scans the beam into optical fibers 124. Each optical fiber terminates in a microlens 126 mounted in a plate 128 of a highly thermal conductive material. Plate 128 also preferably has a highly reflective skin-contacting surface 80. So long as the scan rate of deflector 120 is high enough, the radiation outputted from cylindrical lens 70" or microlenses 126 is CW radiation as this term has been previously defined, and this system operates substantially the same as for previous embodiments. Again, for purposes of simplifying the drawings, elements such as thermal elements 56, motion sensor 78 and 102, and temperature sensors 94, are not shown in FIGS. 12a and 12b.

FIG. 13 is included to illustrate that pre-heating of the treatment area, while more easily facilitated with the CW embodiments heretofore described, is not limited to such embodiments and may be utilized with a standard pulsed head of a type used in some prior art systems. In FIG. 13, radiation, which may be pulsed radiation from a source 30, is applied trough optical lead 32 to an optical waveguide 50 having thermal elements 56 in contact therewith. Waveguide 50, having a focusing skin-contacting end 132, is mounted in a suitable housing, a portion 130 of which is shown in the figure. Thermal elements 56, which are thermoelectric elements, for the embodiment shown, but may be other type of cooling, may be operated to heat waveguide 50 for a time interval sufficient to heat the skin to the depth z of the target. Either the same or a different set of thermoelectric elements 56 may then be operated to cool waveguide 56 for a duration sufficient to cool epidermis 12 to the DE junction 16, at which time source 30 is energized to apply radiation through waveguide 50 to the target. Cooling of waveguide 50 continues during this period to maintain the epidermis at a desired temperature during irradiation and the cooling of waveguide 50 may be contained for some period of time after irradiation terminates to further protect the patient's skin. Further, while preheating has been shown and described above followed by epidermal cooling, and for many applications this is clearly preferable, it is also within the contemplation of the invention to do preheating without subsequent cooling. Head designs such as those shown in FIGS. 2, 4, and 5 (either with or without portion 52, and generally without), 8–12, might also be used when operating in a pulsed mode. Operation with these heads in a pulsed mode could be similar to operation in a CW mode except that movement of the head would be stepped rather than continuous.

While a number of embodiments and variations thereon have been described above, it is apparent that these embodiments are for purposes of illustration only and that numerous other variations are possible while practicing the teachings of this invention. For example, while in the discussion above it has been assumed that head 24 is manually moved over the treatment area, this is not a limitation on the invention and various types of mechanical scanners could also be utilized, either alone or in conjunction with manual control. Further, while optical and kinematic movement measuring mechanisms have been shown, suitable thermal, electronic and magnetic movement measure mechanisms could also be used. Controls 34 would function to maintain the required scan velocity for such scanner. Thus, while the invention has been particularly shown and described above with reference to preferred embodiments, the foregoing and other changes in form and detail may be made therein by one skilled in the art without departing from the spirit and scope of the invention which is to be defined only by the appended claims.

What is claimed is:

1. Apparatus for effecting a selected dermatologic treatment on an area of a patient's skin comprising:
   a source of continuous wave (CW) radiation at a wavelength appropriate for the selected dermatologic treatment;
   a head having at least one optically transparent channel formed therethrough, each said channel having a proximal end connected to receive CW radiation from said source and a distal end terminating in a surface which is smaller than the said area of the patient's skin and which is formed to be in contact with the patient's skin as the head is moved at a selected rate over said area; and
   an indicator of the rate of head movement.

2. The apparatus as claimed in claim 1 further comprising a handle projecting from said head suitable for use by an operator to move the head over the area.

3. Apparatus as claimed in claim 1 wherein said at least one optically transparent channel includes a single elongated channel having an optical channel extending at least partway through the channel and projecting from the bottom of the head.

4. Apparatus as claimed in claim 7 including a component for cooling said optical channel, the cooled optical channel removing heat from the skin in said area under treatment as said optical channel, in thermal contact with the skin, passes thereover.

5. Apparatus as claimed in claim 1 wherein said head is formed to enable an operator of the apparatus to apply at least sufficient pressure to the head as it contacts the skin to assure at least one of good thermal and optical contact between skin-contacting surfaces of the head and the patient's skin in said area.

6. Apparatus as claimed in claim 1 wherein said at least one optically transparent channel includes a plurality of first optical channels angled at a first angle and a plurality of second optical channels angled at a second angle, said first and second angles being selected so that light passing through the first and second optical channels converge at a selected depth.

7. Apparatus as claimed in claim 6 wherein said selected depth is at a depth in the area under treatment at which the dermatological treatment is to occur.

8. Apparatus as claimed in claim 6 including a recess formed in a surface of the head in contact with the patient's skin, said recess being at the distal end of said optical channels, said selected depth being at a selected location in said recess, and including means for moving skin in said area under treatment into said recess as the recess passes thereover.

9. Apparatus as claimed in claim 8 wherein said means for moving skin into said recess includes a source of negative pressure connected to said source.

10. Apparatus as claimed in claim 9 wherein said means for moving skin into said recess includes said recess being shaped to force successive folds of skin therein as the head is moved over said area with said surface of the head in pressure contact with the patient's skin.

11. Apparatus as claimed in claim 9 wherein the apparatus is a hair removal apparatus, and wherein said recess is elongated in a direction perpendicular to the direction in which said head is moved and is sized so as to normally receive therein a fold of the patient's skin which contains several hair follicles extending in the elongated direction.

12. Apparatus as claimed in claim 11 wherein said head has a portion in contact with the patient's skin in segments thereof receiving radiation, and including a thermal component which cools said portion of the head.

13. Apparatus as claimed in claim 1 wherein said transparent channel includes a cylindrical lens.

14. Apparatus as claimed in claim 13 wherein said cylindrical lens is mounted to rotate as said head is moved over said area.

15. Apparatus as claimed in claim 14 wherein said lens is treated so as to normally have total internal reflection, said total internal reflection being broken at a surface of the lens in contact with a patient's skin.

16. Apparatus as claimed in claim 1 including a mechanism for measuring the rate at which said head is being moved over said area.

17. Apparatus as claimed in claim 16 including controls responsive to said mechanism for determining if the head is moving over said area at a rate within a predetermined range and for providing a selected output in response to a determination that the head is moving at a rate outside of said range.

18. Apparatus as claimed in claim 16 including controls responsive to said mechanism for determining if the head is moving at a rate which poses a danger of injury to the patient and for terminating the application of radiation through said at least one channel to the patient's skin in response to a danger-of-injury indication.

19. Apparatus as claimed in claim 1 wherein the distal end of said at least one transparent channel has an astigmatic shape, being narrower in the direction of head movement than in a direction normal thereto.

20. Apparatus as claimed in claim 19 including a mechanism for scanning said CW radiation across said at least one transparent channel.

21. Apparatus as claimed in claim 1 wherein said CW radiation source is a high repetition rate pulse source, the pulse repetition rate (PRR) being such that the delay between pulses is less than the dwell time of the head on said surface contacted by the head (i.e., PRR@V/d, where V=velocity at which head moves and d=dimension of said surface in direction of head movement.

22. Apparatus for effecting a selected dermatologic treatment on a selected volume of a patient's skin located at a depth d which is below the DE junction comprising:

a first mechanism for preheating the patient's skin to raise the selected volume to a selected temperature while not heating any portion of the skin to a temperature sufficient to cause thermal damage thereto;

a second mechanism for cooling the patient's epidermis above said selected volume to a temperature below normal body temperature without resulting in any appreciable cooling of said selected volume; and a third mechanism for applying electromagnetic radiation to said selected volume through said cooled epidermis, the radiation being of a wavelength, energy and duration sufficient, in conjunction with the preheating, to effect thermal damage to at least a selected biological component within said selected volume without causing thermal damage to the cooled epidermis;

wherein said first mechanism includes a source of electromagnetic radiation at a selected wavelength and energy sufficient to cause heating of at least selected biological substances in said selected volume, but not sufficient to cause thermal damage to the patient's skin, and wherein said source of electromagnetic radiation is operable at controllable energy levels and is part of both said first and said third mechanisms at selected energy levels for each.

23. Apparatus for effecting a selected dermatologic treatment on a selected volume of a patient's skin located at a depth d which is below the DE junction comprising:

a first mechanism for preheating the patient's skin to raise the selected volume to a selected temperature while not heating any portion of the skin to a temperature sufficient to cause thermal damage thereto;

a second mechanism for cooling the patient's epidermis above said selected volume to a temperature below normal body temperature without resulting in any appreciable cooling of said selected volume; and a third mechanism for applying electromagnetic radiation to said selected volume through said cooled epidermis, the radiation being of a wavelength, energy and duration sufficient, in conjunction with the preheating, to effect thermal damage to at least a selected biological component within said selected volume without causing thermal damage to the cooled epidermis;

wherein said second mechanism is operative both before and during operation of the third mechanism to protect the epidermis from thermal damage.

24. A head for use in apparatus for effecting a selected dermatologic treatment on an area of a patient's skin including:

a block formed of a material having good thermal transfer properties, a plurality of first optical waveguide elements and a plurality of second optical waveguide elements extending through said block, said first and second optical waveguide elements being angled at first and second angles respectively, which angles are selected so that light passing through the first and second optical waveguide elements converge at a selected depth, said optical waveguide elements having radiation applied thereto appropriate for the selected dermatologic treatment.

25. A head as claimed in claim 24 wherein said selected depth is at a depth in the area under treatment at which the dermatological treatment is to occur.

26. A head as claimed in claim 24 including a recess formed in a surface of the head in contact with the patient's skin, said recess being at the distal end of said optical waveguide elements, said selected depth being at a selected location in said recess, and including means for moving skin in said area under treatment into said recess as said recess passes thereover.

27. A head as claimed in claim 26 wherein said means for moving skin into said recess includes a source of negative pressure connected to said recess.

28. A head as claimed in claim 24 wherein said block has a skin contacting surface which retroreflects radiation leaving the patient's skin.

29. A head as claimed in claim 24 including a mechanism for controlling the temperature of said block.

30. A method for effecting a selected dermatologic treatment on a selected volume of a patient's skin located at a depth d which is below the dermal/epidermal (DE) junction including the steps of:

(a) preheating the patient's skin to raise the selected volume to a selected temperature while not heating any portion of the skin to a temperature sufficient to cause thermal damage thereto;

(b) applying electromagnetic radiation to said selected volume, the radiation being of a wavelength, energy and duration sufficient, in conjunction with the preheating, to effect thermal damage to at least a selected biological component within said selected volume.

31. A head for use in apparatus for effecting a selected dermatologic procedure on an area of a patient's skin comprising:
 an astigmatic optical channel having an elongated outer surface, one side of said surface contacting the patient's skin in said area along an elongated line; and
 a mechanism which delivers light of a wavelength suitable for said dermatologic procedure to said optical channel on a side thereof other than said one side;
 said optical channel focusing light delivered thereto to a selected depth in the patient's skin.

32. The head as claimed in claim 31 wherein said optical channel is a cylindrical lens, and wherein the diameter of the cylindrical lens is such that light delivered thereto is focused to said selected depth.

33. A head as claimed in claim 32 wherein said cylindrical lens is mounted to rotate as said head is moved over said area.

34. The head as claimed in claim 32 wherein said optical channel is treated so as to normally have total internal reflection, said total internal reflection being broken at a surface of the lens in contact with a patient's skin.

35. A head as claimed in claim 32 wherein said lens has a radius of curvature of @ 10 mm.

36. A head as claimed in claim 32 wherein said selected depth is at a depth for a portion of a hair follicle responsible at least in part for hair growth.

37. A head as claimed in claim 42 wherein said selected depth is at approximately the depth of at least one of the hair bulge and the hair bulb.

38. A head as claimed in claim 32 wherein said selected depth is in the range of approximately 1 mm to 5 mm.

39. A head as claimed in claim 33 wherein said mechanism delivers light to said surface along a line substantially parallel to said elongated line.

40. The head as claimed in claim 33 wherein said mechanism causes light to be delivered to said optical channel at a variety of angles.

41. The head as claimed in claim 33 including a cooling mechanism for the patient's skin during at least one of before said optical channel makes contact therewith and while said lens is in contact therewith.

42. A head as claimed in claim 33 wherein said cooling mechanism includes a mechanism for cooling said lens.

43. A head as claimed in claim 33 wherein said selected depth is at a depth for a portion of a hair follicle responsible at least in part for hair growth.

44. A head as claimed in claim 37 wherein said selected depth is at approximately the depth of at least one of the hair bulge and the hair bulb.

45. A head as claimed in claim 37 wherein said selected depth is in the range of approximately 1 nm to 5 nm.

46. The head as claimed in claim 37 wherein said optical channel focuses light at said selected depth to an astigmatic focus area having a long dimension substantially parallel to said elongated line.

47. The head as claimed in claim 37 wherein said mechanism scans said light along said optical channel in its elongated direction, said scanning being at a selected rate.

48. A head for use in apparatus for effecting a selected dermatologic procedure on an area of a patient's skin including:
 a focusing element having a light receiving region, a light delivery region which is adapted to be in contact with the patient's skin, and a region which focuses light entering at said receiving region, the focus, when said element is in contact with the patient's skin, being to an elongated astigmatic focus area at a selected skin depth; and
 a mechanism which delivers light of a wavelength suitable for said dermatologic procedure to said light receiving region.

49. A head as claimed in claim 48 wherein said selected depth is at a depth for a portion of a hair follicle responsible at least in part for hair growth.

50. A head as claimed in claim 35 wherein said selected depth is at approximately the depth of at least one of the hair bulge and the hair bulb.

51. A head as claimed in claim 48 wherein said selected depth is in the range of approximately 1 mm to 5 mm.

52. A head for use in an apparatus for effecting a selected dermatologic treatment on an area of a patients skin comprising:
 an optically transparent channel for delivering optical radiation of a wavelength appropriate for effecting the treatment to said area;
 a head portion of a thermally conductive material mounted relative to said channel so that it moves over each segment to be treated of said area prior to said channel;
 a thermal component which controls the temperature of said portion, and thus of each skin segment, prior to treatment, and
 a block formed of a material having good heat transfer properties, said block being adapted for movement over said area during treatment, said channel being formed through said block, and said portion being a portion of said block which is forward of said channel as said block is moved over said area.

53. A head as claimed in claim 52 wherein said component cools said portion, and thus each said segment prior to treatment.

54. A head as claimed in claim 52 wherein said component heats said portion, and thus each said segment prior to treatment.

55. A head as claimed in claim 52 wherein said portion of the head is divided into a first portion and a second portion which are thermally insulated from each other, said first portion being ahead of said second portion, and wherein said component has a first component which heats said first portion and a second component which cools said second portion.

56. A head as claimed in claim 52 including a rear head portion of a thermally conductive material mounted relative to said channel so that it moves over each segment to be treated of said area after said channel; and
 a thermal component which cools said rear head portion, and thus cools each skin segment after treatment.

57. A head for use in an apparatus for effecting a selected dermatologic treatment on an area of a patients skin including:
 an optically transparent channel for delivering optical radiation of a wavelength appropriate for effecting the treatment to said area;
 a first mechanism operating through said head to heat the patient's skin in said area to a treatment depth; and
 a second mechanism operating through said head after said first mechanism for cooling the patient's skin in said area to approximately the dermis/epidermis (DE) junction, said first and second mechanism being operative before radiation is applied to said channel.

58. Apparatus for effecting a selected dermatologic treatment on an area of a patient's skin comprising:
 a source of continuous wave (CW) radiation at a wavelength appropriate for the selected dermatologic treatment;

a head having at least one optically transparent channel formed therethrough, each said channel having a proximal end connected to receive CW radiation from said source and a distal end terminating in a surface which is smaller than the said area of the patient's skin and which is formed to be in contact with the patient's skin as the head is moved at a selected rate over said area; and a mechanism for measuring the rate at which said head is being moved over said area.

59. The apparatus as claimed in claim 58 further comprising controls responsive to said mechanism for determining if the head is moving over said area at a rate within a predetermined range and for providing a selected output in response to a determination that the head is moving at a rate outside of said range.

60. The apparatus as claimed in claim 58 further comprising controls responsive to said mechanism for determining if the head is moving at a rate which poses a danger of injury to the patient and for terminating the application of radiation through said at least one channel to the patient's skin in response to a danger-of-injury indication.

61. Apparatus for effecting a selected dermatologic treatment on an area of a patient's skin comprising:

a source of continuous wave (CW) radiation at a wavelength appropriate for the selected dermatologic treatment; and a head having at least one optically transparent channel formed therethrough, each said channel having a proximal end connected to receive CW radiation from said source and a distal end terminating in a surface which is smaller than the said area of the patient's skin and which is formed to be in contact with the patient's skin as the head is moved at a selected rate over said area, wherein the distal end of said at least one transparent channel has an astigmatic shape, being narrower in the direction of head movement than in a direction normal thereto.

62. The apparatus of claim 61 wherein the astigmatic shape is oval.

63. Apparatus for effecting a selected dermatologic treatment on an area of a patient's skin comprising:

a source of radiation at a wavelength appropriate for the selected dermatologic treatment;

a head having at least one optically transparent channel formed therethrough, each said channel having a proximal end connected to receive radiation from said source and a distal end terminating in a surface which is smaller than the said area of the patient's skin and which is formed to be in contact with the patient's skin as the head is moved at a selected rate over said area; and an indicator of the rate of head movement.

64. The apparatus of claim 63 wherein the indicator is an audio output device.

65. The apparatus of claim 63 wherein the indicator is a visual output device.

66. The apparatus of claim 63 wherein the indicator is a tactile output device.

67. The apparatus for effecting a selected dermatologic treatment on an area of a patient's skin comprising:

a source of radiation at a wavelength appropriate for the selected dermatologic treatment;

a head having at least one optically transparent channel formed therethrough, each said channel having a proximal end connected to receive radiation from said source and a distal end terminating in a surface which is smaller than the said area of the patient's skin and which is formed to be in contact with the patient's skin as the head is moved at a selected rate over said area; and a mechanism for measuring the rate at which said head is being moved over said area.

68. The apparatus of claim 67 further comprising controls responsive to said mechanism for determining if the head is moving at a rate which poses a danger of injury to the patient and for terminating the application of radiation through said at least one channel to the patient's skin in response to a danger-of-injury indication.

69. The apparatus of claim 67 wherein the distal end of said at least one transparent channel has an astigmatic shape, being narrower in the direction of head movement than in a direction normal thereto.

70. The apparatus of claim 67 wherein the mechanism is a kinematic mechanism.

71. The apparatus of claim 67 wherein the indicator is a thermal mechanism.

72. The apparatus of claim 67 wherein the indicator is a magnetic mechanism.

73. A head for use in an apparatus for effecting a selected dermatologic treatment on an area of a patients skin comprising:

an optically transparent channel for delivering optical radiation of a wavelength appropriate for effecting the treatment to said area;

a head portion of a thermally conductive material mounted relative to said channel so that it moves over each segment to be treated of said area prior to said channel; and a thermal component which controls the temperature of said portion, and thus of each skin segment, prior to treatment;

wherein said component heats said portion, and thus each said segment prior to treatment.

* * * * *